United States Patent
Lair et al.

Patent Number: 5,466,215
Date of Patent: Nov. 14, 1995

[54] METHOD OF USING A CARPAL TUNNEL PROTECTION DEVICE

[75] Inventors: Christopher L. Lair, Wichita, Kans.; Ivan E. Brown, Spirit Lake; Douglas G. Brown, Hartley, both of Iowa

[73] Assignee: Brown Medical Industries, Hartley, Iowa

[21] Appl. No.: 326,038

[22] Filed: Oct. 19, 1994

Related U.S. Application Data

[63] Continuation-in-part of Ser. No. 112,252, Aug. 26, 1993, abandoned.

[51] Int. Cl.[6] .................... A61F 5/00; A41D 19/00
[52] U.S. Cl. .................... 602/21; 602/64; 2/170; 128/878
[58] Field of Search .......... 602/79, 78, 64–60, 602/22–20; 128/880, 879, 878, 882; 2/170

[56] References Cited

U.S. PATENT DOCUMENTS

| | | | |
|---|---|---|---|
| 833,671 | 10/1906 | Brown | 602/79 |
| 883,452 | 3/1908 | Corliss | 602/79 |
| 1,728,679 | 9/1929 | Hansard | |
| 2,496,808 | 2/1950 | Moore | 273/32 |
| 3,062,546 | 11/1962 | Horton et al. | |
| 3,178,724 | 4/1965 | Perschke | 2/16 |
| 3,606,343 | 9/1971 | Lemon | 273/189 R |
| 3,724,458 | 4/1973 | Piper | 602/79 |
| 3,880,426 | 4/1975 | Morse | 273/54 |
| 4,103,682 | 8/1978 | Frazl | 602/22 |
| 4,121,360 | 10/1978 | Vlerebome | 40/586 |
| 4,176,839 | 12/1979 | Pinkus | 602/64 |
| 4,632,105 | 12/1986 | Barlow | 602/64 |
| 4,757,558 | 7/1988 | Strongwater | 2/170 |
| 4,813,406 | 3/1989 | Ogle, II | 128/87 A |
| 4,941,460 | 7/1990 | Working | 128/77 |
| 5,064,198 | 11/1991 | Szabo | 273/189 R |
| 5,101,812 | 4/1992 | Wang | 602/22 |
| 5,135,217 | 8/1992 | Swain | 273/4.5 A |
| 5,188,356 | 2/1993 | Furr et al. | 128/880 |
| 5,346,462 | 9/1994 | Barber | 602/22 |
| 5,348,531 | 9/1994 | Brown et al. | 602/22 |
| 5,370,606 | 12/1994 | Martel et al. | 602/64 |

*Primary Examiner*—Robert A. Hafer
*Assistant Examiner*—Michael O'Neill
*Attorney, Agent, or Firm*—Zarley, McKee, Thomte, Voorhees, & Sease

[57] ABSTRACT

This invention relates to a restraining device to be worn by sufferers of carpal tunnel. The device comprises a wristlet adapted to circle the wrist of a wearer and a flexible and adjustable restraining harness attached to the wristlet for extension over the back of the hand, with the harness terminating in a finger loop for engagement of the base of at least one finger to prevent falling forward of the person's hand.

11 Claims, 1 Drawing Sheet

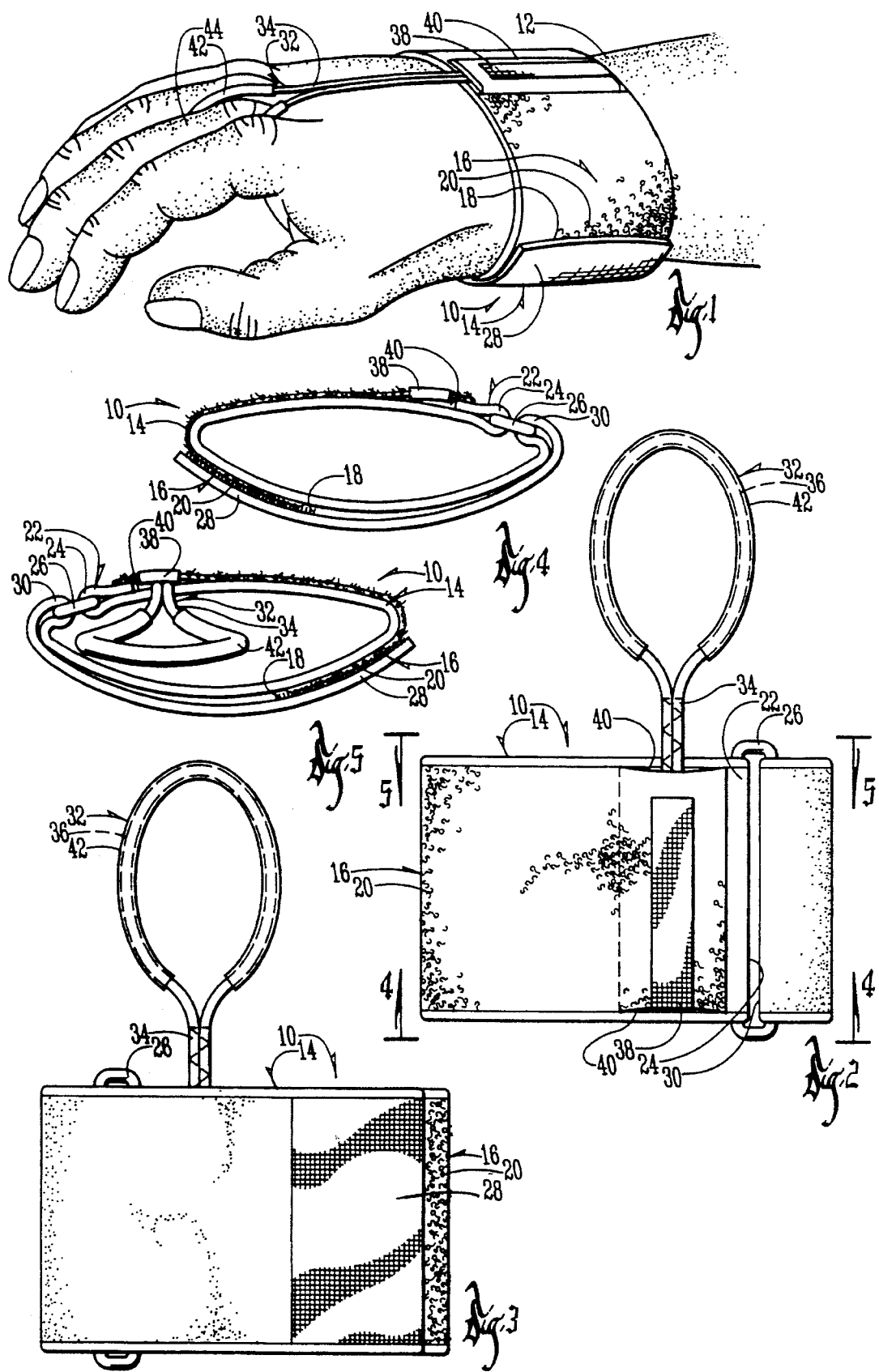

METHOD OF USING A CARPAL TUNNEL PROTECTION DEVICE

CROSS-REFERENCE TO A RELATED APPLICATION

This application is a continuation-in-part of application Ser. No. 08/112,252 filed Aug. 26, 1993, abandoned, and entitled CARPAL TUNNEL PROTECTION DEVICE.

FIELD OF THE INVENTION

This invention relates to the field of medical devices for alleviation of carpal tunnel syndrome, more precisely defined as compressive neuropathy of the median nerve at the wrist.

BACKGROUND OF THE INVENTION

This invention pertains to a device designed to prevent injury or recurrence of carpal tunnel syndrome, particularly after a first incident.

The carpal tunnel problem is one caused primarily by repetitive motions in manual labor, and is exacerbated by the tendency of individuals to sleep in the fetal hand position, causing additional pressure and damage. The pressure on the median nerve inflames the already damaged nerve which passes through the carpal tunnel to the hand.

People suffering from carpal tunnel syndrome experience tingling, numbness and sleeping in their hands and fingers. Often they awaken with pain and numbness. They also lose strength in their hands and fingers. Surgery has been one solution to relieve this pain. With surgery, the carpal tunnel is actually enlarged, resulting in less pressure on the median nerve. Once back and performing the same work, however, people frequently experience a recurrence of the same problems.

A non-surgical solution to carpal tunnel syndrome is use of a restraint that prevents the hand from falling into the fetal position. Previous designs have been of one of two formats. One design is to put a stay in a wrist wrap. The stay is placed on the bottom of the wrist, and the cloth material holding the stay is fastened around the wrist and thumb to hold it in place. One problem with these designs is that the stay, which is placed on the bottom side of the wrist, the most sensitive part of the carpal tunnel area, may actually increase the pain and discomfort of the carpal tunnel. Compliance in the use of this product is low because it is uncomfortable to wear and is encumbering to the hand and, in fact, hurts to wear. Sometimes people choose to suffer with carpal tunnel pain rather than wear such cumbersome devices.

A second and more recent solution is to place the stay on the top of the wrist. This makes more sense because it does not encumber the hand as much as the wrist bottom device. This helps because people are allowed somewhat more freedom of hand and fingers during work. Problems with this device are not as significant as with the stay on the bottom of the wrist, but compliance is still low because the wrist is still immobilized, and the patient's hand so encumbered it is of little use, especially in normal work tasks. In summary, the use of splints to limit wrist motion has been successfully used for treatment of carpal tunnel syndrome in the past, but many of these splints are restrictive, and patients find that they are unable to perform their daily activities. As a result, patient compliance is very low.

In treating carpal tunnel, it is neither necessary nor desirable to eliminate wrist motion completely. There are two particular motions that should be minimized: first, the fetal hand drop; and second, the backflip of the hand. The second occurs much less frequently, so preventing it is not as important as preventing the fetal hand drop, especially during sleep.

In addition to preventing the two particular hand motions, namely fetal hand drop and the backflip of the hand, those must be prevented by a restraining device which is both comfortable to wear and fully adjustable to provide proper fit around the wrist, and to provide finger restraint. In addition, a proper carpal tunnel syndrome restraint must allow the patient to perform normal work tasks with a minimum of interference, must allow the patient to easily wash his or her hands without removal of the restraint, and must not cause chafing either on the wrist or finger. There is no presently available restraining device that provides all of these essential features in an economical and workable carpal tunnel restraining device.

Accordingly, the primary objective of the present invention is to provide a carpal tunnel syndrome treating device which minimizes the motions of fetal hand drop and backflip, which at the same time allows the patient to perform most ordinary daily work tasks with a minimum of interference, and which allows the patient to wash his or her hands while the device is being worn, while at the same time provides a device of maximized comfort and one which causes reduced irritation and chafing of the wrist and fingers, thus increasing the chances of patient compliance with use instructions.

SUMMARY OF THE INVENTION

This invention relates to a restraining device for alleviating symptoms of carpal tunnel syndrome comprised of a wristlet adapted to encircle the wrist of a wearer, and a flexible and adjustable restraining harness attached to the wristlet for extension over the back of the hand, with a restraining harness terminating in a finger loop, having a slidably adjustable comfort sleeve, with the loop end of the sleeve adapted for engagement of the base of at least one finger to prevent the two particular motions that exacerbate carpal tunnel syndrome, namely fetal hand drop and hand backflip.

BRIEF DESCRIPTION OF THE DRAWINGS

FIG. 1 is a perspective view of the restraining device in place on the hand of a user.

FIG. 2 is a plan view of the outer side of the restraint, with the restraint moved from the hand.

FIG. 3 is a view similar to FIG. 2 of the underside of the retainer.

FIG. 4 is an elevated end view along line 4—4 of FIG. 2.

FIG. 5 is an elevated end view along line 5—5 of FIG. 2.

DETAILED DESCRIPTION OF THE INVENTION

Briefly, this invention comprises a retainer adapted to hold one's hand in an open position by holding the base of a finger, for example, the middle finger of that hand. A band around the wrist anchors the retainer to the user. By the present invention, movement of the hand to the fetal hand dropped position is strongly inhibited by simply holding one or more fingers in place. The device may be variably adjustable and is constructed so as to avoid discomfort, especially to the wrist, which is already sore.

More specifically, and referring to the drawings, the restraining device 10 is designed to be worn on the wrist 12 of a user. The wrist band 14 uses a pressure sensitive fastening material 16, such as Velcro®, using mating patches of hooks and loops 18 and 20 at each end of the band. Wrist band 14 has a first end 22 terminating in end loop 24 holding a D-ring 26. Wrist band 14 has a second end 28 which can be inserted through D-ring 26 to define a wrist loop 30 (see FIG. 4). Thus, by grasping at band 14 by its second end 28 after it has been inserted through D-ring 26, one may pull on second end 28 to adjust the dimensions of wrist loop 30 to proper size for the wrist 12 of any patient. D-ring 26 makes for a particularly easy adjustment, since it enhances the slidability of wrist band 14, and once the loops 20 adjacent second end 28 are wrapped back around the band 14 and attached to hooks 18 in a typical Velcro® fastening type manner, the band is securely held in place as illustrated in FIG. 1.

The finger loop of the present invention constitutes one of the significant improvements over the device of our parent application. In particular, with the parent application it was found that the wide finger loop was too encumbering between the fingers, resulting in discomfort, and as a result, considerable chafing at the base of the finger. Moreover, the wide cloth finger loop had a tendency to become soiled and not easily cleanable. In the present invention, the finger loop 32 is defined by a looped cord or string 34, having a loop 36 at its first end, and terminating in an attached Velcro® fastening strap 38 at its second end. Cord 34 fits through wrist band loop 40 so that it may be readily slidably moved transversely at a longitudinal axis of wrist band 14. Thus, the distance between finger loop 32 and wrist band 14 can be controlled by simply pulling strap 38, which is then folded over and engaged to hooks 18 in a conventional Velcro® fastening type manner. Strap 38 can simply be pulled up (see FIG. 2) and readjusted as the patient wishes in order to control the distance between wrist band 14 and finger loop 32. A loop portion 36 of cord 34 is at least partially enclosed by a comfort sleeve 42. Comfort sleeve 42 may be a simple piece of silicone tubing, polyethylene or polypropylene tubing, or any substantially inert plastic material that is easily slidable along cord 34. Importantly, finger loop 32 is defined by a very small diameter cord portion 36, which minimizes the encumbrance of the material between the fingers. Comfort against, for example, circulation cutoff and pressure points is provided by comfort sleeve 42, resulting in less pressure on the base of the finger, less chafing around the finger, and more ease in performing normal work tasks because of the small encumbrance between the fingers.

Although the drawings illustrate use of the restraining device 10 on the middle finger, it is, or should be, readily apparent to those of ordinary skill in the art that another finger, or for that matter a plurality of fingers, might also be used. In fact, if desired, two or more cords 32 may be inserted through the wrist loop 40.

In actual operation, the device can be simply used and quickly installed. The patient simply places finger loop 32 over his or her finger 44, inserts their wrist 12 through wrist loop 30, tightens wrist band 40 by the Velcro type pressure fasteners as above-described, and if needed, adjusts finger loop 30 and attaches it to the Velcro® type fastener pad illustrated at 18 via strap 38. Thus very simply, with a minimum of discomfort, the finger is held substantially in line with the forearm, and the wrist and the hand are held in a comfortable manner to avoid both fetal drop and backflip. As a result, the median nerve is not pinched, but remains open to heal and to avoid reinjury.

This device is much more compatible with daily activities, since it is both lightweight and comfortable. It does restrict excessive flexion of the wrist, but at the same time allows some wrist flexion to occur within the functional ranges necessary to perform most daily activities, and thus it can be worn during work or home tasks. The loop feature around the middle finger, especially with its adjustability for length, and the small diameter cord, coupled with the comfort sleeve 42, allows complete freedom and access to the palm for both work use and for patient washing of the hand. The restraint 10 is fully adjustable, and patients generally find it much more comfortable to wear than rigid splints worn on either the top of the hand or the bottom of the hand. At the same time the device is far less expensive than more complex splints, and avoids all of the disadvantages of a simple cord or strap across the base of the finger by relieving the tendency of such to cause excessive pressure, chafing and irritation. Thus it can be seen that the device provides a lightweight, comfortable restrainer which makes patient compliance far more likely. As illustrated in FIG. 1, damaging wrist flexion is avoided, but at the same time a healthy range of motion is provided, while the finger and hand are essentially allowed a full range of grasping capability enhancing likelihood of full productivity at work.

What is claimed is:

1. A method of protecting a person against carpal tunnel syndrome comprising treating a person with carpal tunnel syndrome:

providing said person with a wristlet adapted to encircle the wrist of said person and adjustably fastenable by a D-ring;

engaging the base of at least one finger on the hand adjacent to said wrist with a finger loop end of a flexible restraining harness strap of small diameter cord, said strap being attached to said wristlet, said finger loop having a comfort sleeve of inert polymeric plastic material and;

adjusting said harness strap so that said one finger is restrained and said hand is restrained to restrict excessive flexion of the wrist, but at the same time allows some wrist flexion to occur within the functional ranges necessary to perform most daily activities, thus restraining said hand from fetal drop and from backflip, while still allowing full finger movement so that the median nerve remain open.

2. The method of claim 1 further comprising the step of adjustably fastening said wristlet about said wrist.

3. The method of claim 2 wherein said step of adjustably fastening said wristlet is accomplished by a hook and loop fastener.

4. The method of claim 2 wherein said step of adjusting said harness strap is by means to allow adjustment of patches of pressure sensitive fastening material.

5. The method of claim 1 wherein said step of engaging at least one finger includes engaging the middle finger.

6. The method of claim 5 wherein said step of engaging at least one finger includes engaging only the middle finger.

7. A method of protecting a person against carpal tunnel syndrome comprising treating a person with carpal tunnel syndrome:

providing said person with an adjustably fastenable wristlet adapted to encircle the wrist of said person;

fastening said wristlet about said wrist;

engaging the base of at least one finger on the hand adjacent to said wrist with a finger loop end of a flexible restraining harness strap of small diameter cord, said strap being attached to said wristlet, and said finger loop having a comfort sleeve of inert polymeric plastic material and;

adjusting said harness strap so that said one finger is restrained and said hand is restrained to restrict excessive flexion of the wrist, but at the same time allows some wrist flexion to occur within the functional ranges necessary to perform most daily activities, thus restraining said hand from fetal drop and from backflip, while still allowing full finger movement so that the median nerve remain open.

8. The method of claim 7 wherein said step of adjustably fastening said wristlet is accomplished by a hook and loop fastener.

9. The method of claim 8 wherein said step of adjustably fastening said wristlet is by a D-ring.

10. The method of claim 7 wherein said step adjusting said harness strap is accomplished by means to allow adjustment of patches of pressure sensitive fastening material.

11. A method of protecting a person against carpal tunnel syndrome comprising treating a person with carpal tunnel syndrome:

providing said person with a wristlet adapted to encircle the wrist of said person and adjustably fastenable by a D-ring;

engaging the base of at least one finger on the hand adjacent to said wrist with a finger loop end of a flexible adjustable restraining harness strap of small diameter cord, said strap being attached to said wristlet; and adjusting said harness strap so that said one finger is restrained and said hand is restrained to restrict excessive flexion of the wrist, but at the same time allows some wrist flexion to occur within the functional ranges necessary to perform most daily activities, thus restraining said hand from fetal drop and from backflip, while still allowing full finger movement so that the median nerve remain open.

* * * * *